United States Patent
Kushnir et al.

[11] Patent Number: 6,166,081
[45] Date of Patent: Dec. 26, 2000

[54] METHODS AND APPARATUS FOR TREATMENT OF PARKINSON'S DISEASE

[76] Inventors: Moshe Kushnir, 5 Jericho St., Ramat Gan 52356; Eliahu Heldman, 8 Simtat Hamuchtar, Rehovot 76516, both of Israel

[21] Appl. No.: 09/287,951

[22] Filed: Apr. 7, 1999

Related U.S. Application Data

[63] Continuation of application No. PCT/IL97/00327, Oct. 9, 1997.

[51] Int. Cl.⁷ ............ A61K 31/195; A61K 31/135; C07C 271/06
[52] U.S. Cl. ............ 514/567; 514/649; 560/38; 560/42; 562/442
[58] Field of Search ............ 560/38, 42; 514/567, 514/649; 562/442

[56] References Cited

U.S. PATENT DOCUMENTS 5,354,885  12/1995  Milman et al. ............ 560/43
5,474,783  12/1995  Miranda et al. ............ 424/448

*Primary Examiner*—Cecilia Tsang
*Assistant Examiner*—Ebenzer Sackey
*Attorney, Agent, or Firm*—Stroock & Stroock & Lavan LLP

[57] ABSTRACT

A pharmaceutical composition for treatment of Parkinson's disease comprising a compound of levodopa dissolved in a non-degradative solvent which allows transdermal administration of levodopa. The compound of levodopa is an alkyl-ester of levodopa and the solvent is a formulation comprising a substantially non-aqueous solvent, a transdermal enhancer and a detergent. The alkyl-ester of levodopa is preferably levodopa-ethyl-ester (LDEE).

12 Claims, 2 Drawing Sheets

METHODS AND APPARATUS FOR TREATMENT OF PARKINSON'S DISEASE

This Application is a continuation of International Application No. PCT/IL97/00327, filed Oct. 9, 1997.

FIELD OF THE INVENTION

The present invention relates to methods and apparatus for treatment of Parkinson's disease.

BACKGROUND OF THE INVENTION

Parkinson's disease (PD) is one of the most common neuro-degenerative diseases which affect the elderly.

The following is a representative list of references which discuss Parkinson's disease and therapeutic strategies:

1. de Rijk M C, Breteler M M B, Graveland G A, et al. Prevalence of Parkinson's disease in the elderly: The Rotterdam study. Neurol. 1995; 45:2143–2146.
2. Bennet D A, Beckett L A, Murray A M, et al. Prevalence of Parkinsonian signs and associated mortality in a community population of older people. N Engl. J. Med. 1996; 334(2):71–76.
3. Hornykiewicz O, Kish S J. Biochemical pathophysiology of Parkinson's disease. Adv Neurol. 1986; 45:19–34.
4. Leenders K L, Salmon E P, Tyrrel P, et al. The nigrostriatal dopaminergic system assessed in vivo by positron emission tomography in healthy volunteer subjects and patients with Parkinson's disease. Arch Neurol. 1990; 47:1290–1298.
5. LeWitt P A. Levodopa Therapeutics: New treatment strategies. Neurology 1993; 43(suppl. 6):S31–S37.
6. Peppe A, Dambrosia J M, Chase T N. Risk factors for motor response complications in L-Dopa treated parkinsonian patients. Adv Neurol 1993; 60:698–702.
7. Chase T N, Mouradian M M, Engber T M. Motor response complications and the function of striatal efferent systems. Neurology 1993; 43(suppl. 6): S23–S27.
8. Doller H J, Connor J D. Changes in neostriatal dopamine concentrations in response to levodopa infusions. J Neurochem 1980; 34:1264–1269.
9. Spencer S E, Wooten G F. Altered pharmacokinetics of L-dopa metabolism in rat striatum deprived of dopaminergic innervation. Neurology 1984; 34:1105–1108.
10. Spencer S E, Wooten G F. Pharmacologic effects of L-dopa are not closely linked temporally to striatal dopamine concentration. Neurology 1984; 34:1609–1611.
11. Hardie R J, Malcolm S L, Lees A J, et al. The pharmacokinetics of intravenous and oral levodopa in Parkinson's patients who exhibit on-off fluctuations Br J Clin Pharmacol 1986; 22:421–436.
12. Fabbrini G, Juncos J, Mouradian M M, et al. Levodopa pharmacokinetic mechanisms and motor fluctuations in Parkinson's disease. Ann Neurol 1987; 21:370–376.
13. Nutt J G, Woodward W R, Hammerstad J P, et al. The "on-off" phenomenon in Parkinson's disease: relation to levodopa absorption and transport. N Engl J Med 1984, 310:483–488.
14. Shoulson I, Glaubiger G A, Chase T N. On-off response: clinical and biochemical correlations during oral and intravenous levodopa administration in parkinsonian patients. Neurology 1975; 25:1144–1148.
15. Quinn N, Parkes J D, Marsden C D. Control of on/off phenomenon by continuous intravenous infusion of levodopa. Neurology 1984; 34:1131–1136.
16. Schuh L A, Bennet J P. Suppression of dyskinesias in advanced Parkinson's disease. I. Continuous intravenous levodopa shifts dose-response for production of dyskinesias but not for relief of parkinsonism in patients with advanced Parkinson's disease. Neurology 1993; 43:1545–1550.
17. Sage J I, McHale DM, Sonsulla P, et al. Continuous levodopa infusion to treat complex dystonia in Parkinson's disease. Neurology 1989; 39:888–891.
18. Schelosky L, Poewe W. Current strategies in the drug treatment of advanced Parkinson's disease—new modes of dopamine substitution. Acta neurol Scand 1993; 87(suppl. 146):46–49.
19. Nutt J G, Woodward W R. Levodopa pharmacokinetics and pharmacodynamics in fluctuating parkinsonian patients. Neurology 1986; 36:739–744.
20. Nelson M V, Berchou R C, LeWitt P A, et al. Pharmacodynamic modeling of concentration-effect relationship after controlled-release carbidopa/levodopa (Sinemet CR-4) in Parkinson's disease. Neurology 1990; 40:70–74.
21. Bredberg E, Nilson D, Johansson K, et al. Intraduodenal infusion of a water-based levodopa dispersion for optimisation of the therapeutic effect in sever Parkinson's disease. Eur J Clin Pharmacol 1993; 45:117–122.
22. Mouradian M M, Juncos J L, Fabbrini G, et al. Motor fluctuations in Parkinson's disease: central pathophysiological mechanisms. Part II. Ann Neurol 1988; 24;372–378.
23. Sage J I, Mark M H. The rationale for continuous dopaminergic stimulation in patients with Parkinson's disease. Neurology 1992; 42(Suppl. 1):23–28.
24. Chase T N Baronti F, Fabbrini G, et al. Rational for continuous dopaminometic therapy of Parkinson's disease. Neurology 1989; 39(Suppl. 2):7–10.
25. Sage J I, Mark M I. Basic mechanisms of motor fluctuations. Neurology 1994; 44(Suppl. 6):S10–S14.
26. Sage J L, Trooskin S, Sonsalla P K, et al. Experience with continuous enteral levodopa infusions in the treatment of 9 patients with advanced Parkinson's disease. Neurology 1989; 39(Suppl. 2):60–63.
27. Mouradian M M, Heuser I J E, Baronti F, et al. Modification of central dopaminergic mechanisms by continuous levodopa therapy for advanced Parkinson's disease. Ann Neurol 1990; 27:18–23.
28. Bravi D, Mouradian M M, Roberts J W, et al. End-of-dose dystonia in Parkinson's disease. Neurology 1993; 43:2130–2131.
29. Tanner C M, Melamed E, Lees A J. Managing motor fluctuations, dyskinesias and other adverse effects in Parkinson's disease. Neurology 1994; 44(Suppl. 1):S12–S16.
30. Joseph King Ching Tsui. Future Treatment of Parkinson's disease. Can J Neurol Science 1992; 19:160–162.
31. Djaldetti R, Atlas D, Melamed E. Subcutaneous injections of levodopa-ethylester: A potential novel rescue therapy for response fluctuations in patients with Parkinson's disease (Abst). Neurology 1995; 45(Suppl. 4):415S.
32. LeWitt P A. In: Levodopa controlled-release preparations. Neurology 1993, 43(Suppl. 6)S38–S40.
33. Koller W C, and Pahwa R. Treating motor fluctuations with controlled-release levodopa preparations. Neurology 1994; 44(Suppl. 6):S23–S28.

The prevalence of diagnosed PD in the population above the age of 55 is about 1.4% and it increases with age (Ref. 1). Moreover, Parkinsonian signs in the elderly are estimated to occur in 30% of the population over the age of 65 (Ref. 2). Although PD is considered a multisystem disease, it is mainly a movement disorder caused by a continuous, long lasting degeneration of the dopaminergic neurons that are located in the mesencephalic substantia nigra pars compacta. PD becomes symptomatic only after degeneration of about 60–80% of these dopaminergic neurons, or after the loss of about 90% of the striatal dopamine (Refs. 3, 4). Dopamine (DA), which is produced within the substantia nigra, reaches the striatum via the nigro-striatal tract and is released at the striatal synapses. DA deficiency in the striatum, due to the degeneration of the dopaminergic neurons in the substantia nigra, is considered to be the cause of PD. Consequently, the most effective treatment of PD is Levodopa (LD), which is converted to DA by enzymatic decarboxylation. Inhibition of the peripheral aromatic amino acid decarboxylase by carbidopa (an inhibitor that cannot penetrate the blood-brain-barrier) improves dramatically the results of the treatment. However, the currently available LD preparations are effective only for a relatively short period and may be even deleterious under certain conditions (as will be explained below).

Administration of LD is especially successful during early stages of the disease. Adverse effects of LD, such as dyskinesias and hallucinations that occur at early stages of the disease are dose-dependent. These adverse effects are attributed to hypersensitivity of denervated striatal dopaminergic receptors to exogenous doparmine (Ref. 5). At late stages of the disease additional types of adverse effects appear as the response to LD becomes unpredictable, fluctuative and the duration of the response is reduced. Motor fluctuations appear after about 4–5 years from the introduction of LD therapy in 24%–84% of the patients (Ref. 6). The most common and disabling motor complications are: 1) "wearing-off" fluctuations; 2) "on-off" fluctuations and 3) peak-dose dyskinesias (Ref. 7).

The "wearing-off" effect means a reduction in the duration of the beneficial effect after each administration of LD. During this period, LD must be administered more frequently than before, a problem which severely affects the quality of life of the patient. Complications such as "wearing off" may arise due to limitation of storage capacity of DA in the CNS (Refs. 5, 8–10). When neuronal DA storage is reduced, the clinical state of the patients becomes fully dependent on the fluctuating blood level of LD. Since the normal half-life of LD in the circulation is 1–2 hours (Refs. 11–13), LD should be administered at this stage more frequently and the effect is fluctuative. Moreover, with the currently available oral preparations, the blood level of LD is a function of the rate of absorption from the gastrointestinal tract, which is irregular and uncontrollable. The resulting fluctuations of the LD blood levels contribute further to the instability of the effect. A continuous drug delivery, which maintains a constant blood level of LD, has been shown to improve significantly the clinical state of the fluctuating parkinsonian patients (Refs. 13–18). In this regard, it has been reported that therapeutic effects of LD were noticed when LD plasma levels reached 300–800 ng/ml (Refs. 19–21).

The "on-off" fluctuations are inconsistent transitions between a hypokinetic parkinsonian state (the "off" state) and a hyperkinetic state (the "on" state). The clinical state of these patients is highly correlated with the plasma concentration of LD (Refs. 5, 20). It is thought that these fluctuations result from a narrowing of the therapeutic window of LD. An intermittent administration of LD, given for a long period, is considered to be one of the major causes of the reduction of the therapeutic window (Refs. 22, 23) and consequently leads to the motor fluctuations (Refs. 23–25). On the other hand, a continuous infusion of LD has been shown to increase the therapeutic window and to reduce the "on-off" fluctuations (Refs. 25–27). Moreover, during a continuous administration, the blood levels of LD which are needed to keep the patient at the "on" state gradually decrease (Ref. 21).

Peak-dose dyskinesia is a common advanced motor complication which occurs when the blood level of LD rises to its peak. This complication is observed in advanced stages of the disease when patients show a very steep dose-response curve. Under such circumstances, small shifts in circulating LD levels, and thus in cerebral DA, induce major swings in the clinical state (Ref. 7). In this stage of the disease, a continuous administration that keeps the circulating LD level constant, may prevent the dyskinesias. Moreover, these kinds of dyskinesias, like the "on-off" dyskinesia, may not develop during a continuous administration of LD (Refs. 7, 16, 17, 28, 29).

All these findings and observations clearly suggest that a continuous delivery of LD is advantageous over an intermittent administration. Persistent attempts have been made in effort to develop a sustained delivery of LD (Refs. 30, 31). Strategies to improve the clinical results of intermittent LD administration include controlled release (CR) preparations and pump-delivery of LD. However, the existing preparations and devices suffer from several disadvantages as follows:

1. CR preparations have a delayed onset. The peak effect of Sinemet CR (commercially available from Merck Sharp and Dohme Research Laboratories) was shown to occur an hour later than that of the conventional Sinemet (Refs. 18, 32).
2. The bioavailability of the CR preparations is low (Refs. 18, 32). The low bioavailability is explained by the variable properties of the gastro-intestinal tracts (Ref. 33).
3. Reduced reliability and predictability of the clinical response (Refs. 32, 33).
4. According to many investigators, the CR preparations do not provide the same favorable effect which was demonstrated by a continuous administration of LD such as an IV infusion (e.g., Refs. 5, 15, 18).
5. Sclerosis of the peripheral veins occurs frequently during an IV infusion of LD (Ref. 5).
6. A gastrostom-duodenal tube or an esophageal catheter is very unpleasant.

To overcome these disadvantages, and yet to administer LD in a continuous manner, an alternative method of drug delivery is needed.

SUMMARY OF THE INVENTION

In the present invention, we claim that transdermal delivery of LD could be the best substitution for the methods of continuous invasive infusions, free of disadvantages of the currently available strategies:

The present invention constitutes a solution to most of the problems associated with the currently available treatments, and thus provides a safer and more effective treatment for PD.

The invention describes a novel route of administration of levodopa dissolved in a formulation which is designed to maintain stability of the drug in solution and enables continuous penetration of the drug through the skin. This method is suggested as a treatment of Parkinson's patients, especially at advanced stages of the disease. The currently available LD preparations cause side effects and deterioration in the clinical state of the disease. The present invention helps overcome these disadvantages.

In accordance with a preferred embodiment of the present invention, an alkyl-ester of LD such as levodopa-ethyl-ester (LDEE) is administered transdermally. For this purpose, the alkyl-ester of LD is dissolved in an appropriate formulation. The formulation consists of propylene glycol, a fatty acid and a detergent. The LD-alkyl-ester and the formulation (the solvent) are kept separately and mixed just before the beginning of the drug application. A transdermal device which includes a container connected to a patch via a narrow plastic tube is used for the transdermal delivery. The container is re-filled every 24 h. The patch is fed with the LD-alkyl-ester solution preferably by gravity, or alternatively by pump, the solution then being spread on the skin area covered by the patch. During treatment, the patient ingests tablets of carbidopa (25–50 mg/tablet) three times a day. According to the clinical needs, the patient could receive a supplemental treatment such as oral anti-parkinson's drug.

BRIEF DESCRIPTION OF THE DRAWINGS

The present invention will be understood and appreciated more fully from the following detailed description, taken in conjunction with the drawings in which.

DETAILED DESCRIPTION OF A PREFERRED EMBODIMENT

A formulation (solvent) useful in transdermal treatment of Parkinson's disease, in accordance with a preferred embodiment of the present invention, is now described.

The formulation is designed to dissolve a treating drug (alkyl-ester of LD) and maintain it stable in solution for the period during which a continuous transdermal penetration takes place. Preferably, the formulation provides the drug with stability and transdermal permeation properties. To achieve these goals, the formulation preferably contains several components as follows:

1) Non-aqueous solvent

LD and its derivatives are more stable in non-aqueous solution than in aqueous solution. A preferred solvent is propylene glycol which is non-toxic, does not produce skin irritation and provides the proper constituency for dermal application. Other non-aqueous solvents with similar properties may also be used for this purpose.

2) Transdermal enhancer and stabilizer

A preferred transdermal enhancer and stabilizer is carboxylic acid. The alkyl-esters of LD are quite soluble and much more stable in an acidic environment than in a neutral environment. The carboxylic acid also keeps the LD derivative uncharged and helps permeability through the skin.

3) Detergent

Detergents have been shown to be transdermal enhancers. The detergent should not interfere with the chemical stability of the penetrating drug and should not be toxic. We found that sodium laurylsulphate and sodium deoxycholate are adequate detergents for the purpose of transdermal delivery of LD. Yet, other detergents may also be appropriate for this purpose.

Figure 1:
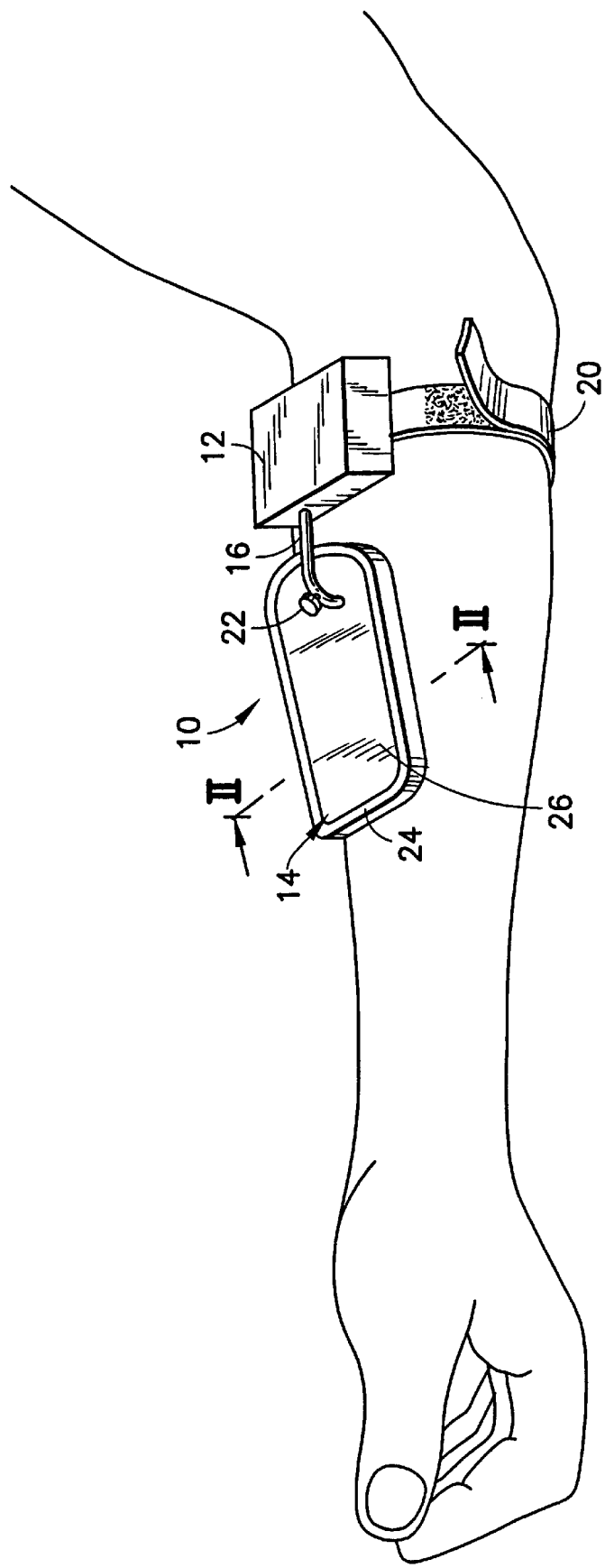
FIG. 1 is a simplified pictorial illustration of apparatus for transdermal administration of levodopa, constructed and operative in accordance with a preferred embodiment of the present invention.
Figure 2:
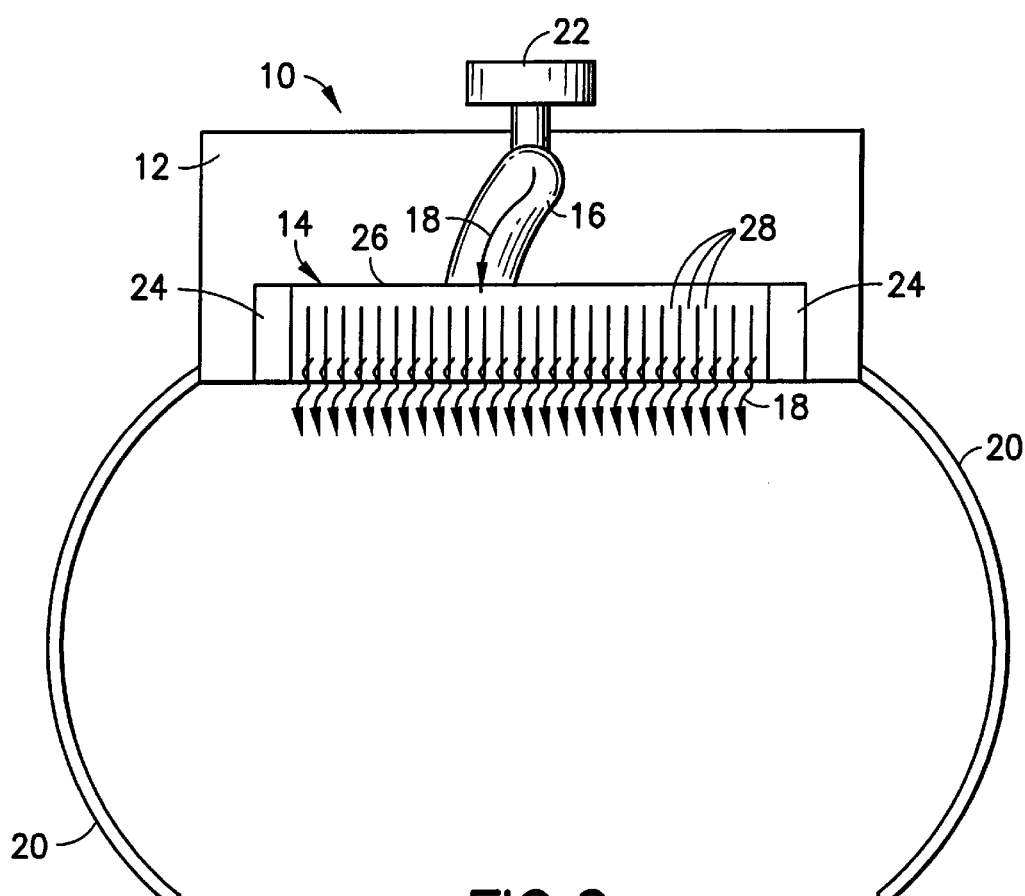
FIG. 2 is a simplified sectional illustration of apparatus of FIG. 1, taken along the lines II—II in FIG. 1.

Reference is now made to FIGS. 1 and 2 which illustrate apparatus 10 for transdermal administration of levodopa, constructed and operative in accordance with a preferred embodiment of the present invention.

Apparatus 10 preferably includes a storage compartment 12 which is in fluid communication with a dermal patch 14, preferably via a flexible plastic tube 16. Patch 14 may be made of any suitable material, such as cloth or plastic. Storage compartment 12 is preferably flexible and compressible by mechanical pressure. Storage compartment 12 preferably contains a fluid 18 (FIG. 2) which is a treating drug, such as an alkyl-ester of LD, dissolved in a formulation, such as described hereinabove in accordance with a preferred embodiment of the present invention.

In accordance with a preferred embodiment of the present invention, the alkyl-ester of LD is kept pre-weighed as a dried powder. Carbidopa (25–50 mg/tablet) is preferably ingested two hours before the beginning of the transdermal delivery of the LD derivative and then three times a day throughout the entire treatment. Preferably just before the beginning of the dermal application, the alkyl-ester of LD is placed in storage compartment 12 and a sufficient amount of formulation is added therein, and the constituents are thoroughly mixed together. Storage compartment 12 is then preferably tied to an arm or any other suitable location on a patient, such as with a strap 20, and connected to patch 14 via tube 16.

Flow of fluid 18 from storage compartment 12 to patch 14 is preferably controlled by a regulating valve 22. Patch 14 is preferably attached to the skin along an adhesive periphery 24, and a central portion 26 is preferably adapted to receive and maintain a quantity of fluid 18. Fluid 18 spreads under patch 14 preferably via a system of hollow capillaries 28 (FIG. 2), and penetrates the skin of a patient.

In a normal mode of application, fluid 18 flows from storage compartment 12 to patch 14 by gravity, or alternatively by a miniature pump (not shown). When necessary, flow of fluid 18 may be increased by exerting mechanical pressure on storage compartment 12 or by increasing the pump rate.

Apparatus 10 is preferably disposable. The location of apparatus 10 on the patient's skin may be changed periodically. Supplemental oral treatment may be given during the transdermal delivery according to clinical needs.

Various preparations of LD have been tested by the inventors and the experimental results are now presented.

Solubility of LDEE: The solubility of LD, LD methyl ester (LDME) and LD ethyl ester (LDEE) was examined in several potential solvents, with increasing amounts of the three LD derivatives being added to a constant volume of 5% propionic acid in water or 10% propionic acid in propylene glycol. We found that only negligible amounts of LD or LDME were soluble in the two solvents, whereas at least 660 mg LDEE were soluble in 1 ml of both solvents. Adding 33% glycerol to the aqueous solvent did not significantly alter the solubility of the three derivatives, although a higher concentration of propionic acid (10%) was needed in the case of the aqueous solutions.

Stability of LDEE: The stability of LDEE was tested in several combinations of potential components of the formulation. For this purpose, 500 mg LDEE was dissolved in 1 ml 5% propionic acid just before the beginning of the stability experiment. In parallel, 500 mg LDEE was dissolved in 1 ml propylene glycol containing 10% propionic acid. These preparations of LDEE were used as stock solutions for several tested formulations as follows:

1) LDEE in aqueous solution of 5% propionic as prepared above.
2) Same solution as in No. 1 above+5% sodium deoxycholate.
3) Same solution as in No. 1 above+5% sodium dodecylsulfate.
4) Same solution as in No. 1 above+5% Tween-20.

5) Same solution as in No. 1 above+5% tritonX100.
6) Same solution as in No. 1 above+glycerol at a ratio of 1:1.
7) Same solution as in No. 1 above+propylene glycol at a ratio of 2:1.
8) LDEE in propylene glycol containing 10% propionic acid.
9) Same solution as in No. 8 above+5% sodium deoxycholate.
10) Same solution as in No. 8 above+5% sodium dodecylsulfate.

The above LDEE formulations were run on a thin layer chromatography (on silica gel—Merk Art. 5735; and on cellulose—Merk Art. 5574) for a qualitative detection of LDEE and its degradative products. The various LDEE formulations were kept at room temperature for several days and separation of the LDEE and its degradative products on the thin layer chromatography were repeated at various times after dissolving the LDEE. The running solvents for the thin layer chromatography were:

a) Propanol: Butanoic Acid: Water (20:4:10).
b) Dichloromethane: Acetone: Ethyl-Acetate: Methanol (35:15:1:0.25).

Immediately after the preparation, LDEE appeared on the thin layer chromatography as a single spot. No degradative products were seen at this stage. Degradative products appeared in formulations that contained tritonX100 24 h after dissolving the LDEE. Other formulations did not show significant degradation 24 h after dissolving the LDEE. At 48 h after dissolving the LDEE, degradative products appeared in all the aqueous solutions with the following order of degradation: formulation containing tritonX100>formulation containing Tween-20>formulation containing sodium dodecylsulfate=formulation containing sodium deoxycholate. In the propylene glycol-based formulations, the LDEE was stable for more than 48 h.

Pharmacolanetic study: In a pilot experiment of transdermal delivery, two human volunteers were exposed for 24 h to LDEE dissolved in propylene glycol containing 10% propionic acid and 5% of either sodium deoxycholate (one volunteer) or sodium dodecylsulfate (one volunteer). Blood samples were taken at various times after the application of the LDEE on the skin and LDEE in the serum was separated on high performance liquid chromatography and determined with an electrochemical detector. The protocol and the details of this pilot study are described in the enclosed appendix. The results showed that blood levels of LDEE after dermal application using the above mentioned formulations could reach about 200 ng/ml. These levels are considered appropriate for obtaining therapeutic effect in Parkinson's patients.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. A pharmaceutical composition for treatment of Parkinson's disease comprising a compound of levodopa dissolved in a non-degradative solvent which allows transdermal administration of levodopa wherein said compound of levodopa is an alkyl-ester of levodopa and said solvent is a formulation comprising a substantially non-aqueous solvent, a transdermal enhancer and a detergent.

2. A pharmaceutical composition according to claim 1 wherein said alkyl-ester of levodopa is levodopa-ethyl-ester (LDEE).

3. A pharmaceutical composition according to claim 1 wherein said non-aqueous solvent has at least one of the following properties: non-toxic and non-irritant.

4. A pharmaceutical composition according to claim 1 wherein said non-aqueous solvent is propylene glycol.

5. A pharmaceutical composition according to claim 1 wherein said transdermal enhancer is also a stabilizer.

6. A pharmaceutical composition according to claim 1 wherein said transdermal enhancer is a carboxylic acid.

7. The pharmaceutical composition according to claim 6 wherein said carboxylic acid is selected from the group consisting of propionic acid and butanoic acid.

8. A pharmaceutical composition according to claim 1 wherein said detergent is selected from the group consisting of sodium laurylsulphate, sodium deoxycholate and their derivatives.

9. A method for treatment of Parkinson's Disease, comprising the steps of transdermally administering a levodopa drug in a stable solution and the step of receiving an oral anti-parkinson's drug wherein said compound of levodopa is an alkyl-ester of levodopa and said solvent is a formulation comprising a substantially non-aqueous solvent, a transdermal enhancer and a detergent.

10. The method according to claim 9 wherein said anti-Parkinson's drug is a decarboxylase inhibitor selected from the group consisting of:
   a) carbidopa; and
   b) benesaride.

11. The method according to claim 10 wherein said carbidopa is taken orally in a dosage of at least 25 mg daily.

12. A pharmaceutical composition according to claim 1 wherein said LDEE is mixed with said substantially non-aqueous solvent, said transdermal enhancer and said detergent to form said pharmaceutical composition immediately prior to transdermally administration.

* * * * *

UNITED STATES PATENT AND TRADEMARK OFFICE
CERTIFICATE OF CORRECTION

PATENT NO. : 6,166,081
DATED : December 26, 2000
INVENTOR(S) : Moshe Kushnir and Eliahu Heldman It is certified that error appears in the above-identified patent and that said Letters Patent is hereby corrected as shown below:

Claims,
1. A pharmaceutical composition for treatment of Parkinson's disease comprising a compound of levodopa in a non-degradative solvent which allows transdermal administration of levodopa wherein said compound of levodopa is an alkyl-ester of levodopa and said solvent is a formulation comprising a [substantially] non-aqueous solvent, a transdermal enhancer and a detergent.

9. A method for treatment of Parkinson's Disease, comprising the steps of transdermally administering a levodopa drug in a stable solution and the step of receiving an oral anti-Parkinson's drug wherein said compound of levodopa is an alkyl-ester of levodopa and said [solvent] solution is a formulation comprising a [substantially] non-acqueous solvent, a transdermal enhancer and a detergent.

12. A pharmaceutical composition according to claim 3 wherein said LDEE is mixed with said [substantially] non-aqueous solvent, said transdermal enhancer and said detergent to form said pharmaceutical composition immediately prior to transdermally administration.

Signed and Sealed this

Ninth Day of April, 2002

*Attest:*

JAMES E. ROGAN
*Attesting Officer*  *Director of the United States Patent and Trademark Office*